(12) United States Patent
Brent et al.

(10) Patent No.: US 7,615,098 B2
(45) Date of Patent: Nov. 10, 2009

(54) METHOD FOR DETERMINING STICKING AND FLOW PROPERTIES OF PARTICULATE SOLIDS

(75) Inventors: Allon Dudley Brent, Duncraig (AU); Peter Leonard John Mayfield, Hamilton (AU); Dean Page Crawford, Medowie (AU); Thomas Alexander Honeyands, Tingira Heights (AU); Andrew Shook, Eleebana (AU); Damien O'Dea, Redhead (AU)

(73) Assignee: BHP Billiton Innovation Pty. Ltd. (AU)

( * ) Notice: Subject to any disclaimer, the term of this patent is extended or adjusted under 35 U.S.C. 154(b) by 341 days.

(21) Appl. No.: 11/025,339

(22) Filed: Dec. 29, 2004

(65) Prior Publication Data

US 2005/0109160 A1    May 26, 2005

Related U.S. Application Data

(62) Division of application No. 10/451,093, filed as application No. PCT/AU01/01657 on Dec. 21, 2001, now Pat. No. 6,845,680.

(30) Foreign Application Priority Data

Dec. 22, 2000    (AU) .................................. PR2289

(51) Int. Cl.
    *C21B 11/00*    (2006.01)
(52) U.S. Cl. .......................................... 75/443; 73/866

(58) Field of Classification Search .................. 75/449, 75/380, 443; 73/866
See application file for complete search history.

(56) References Cited

U.S. PATENT DOCUMENTS

| 3,940,997 A | 3/1976 | Hudson |
| 4,697,463 A | 10/1987 | Spooner et al. |
| 6,158,293 A | 12/2000 | Poole |
| 6,845,680 B2 * | 1/2005 | Brent et al. .................. 73/866 |

FOREIGN PATENT DOCUMENTS

| JP | 183289 | 7/2001 |
| SU | 451940 | 11/1974 |

* cited by examiner

*Primary Examiner*—George Wyszomierski
*Assistant Examiner*—Weiping Zhu
(74) *Attorney, Agent, or Firm*—Brinks Hofer Gilson & Lione; G. Peter Nichols

(57) ABSTRACT

A method of obtaining a measure of the stickiness of heated particulate solids (40) includes pouring a sample of the particulate solids (40) onto a generally horizontal support (12) and allowing it to freely form its own angle of repose. The sample is subjected to a predetermined heat and gas atmosphere regime, and the support is rotated about a generally horizontal axis to an angle (42) where the integrity of the sample (40) fails. The angular position (42) is a measure of the stickness of the particulate solid (40).

7 Claims, 4 Drawing Sheets

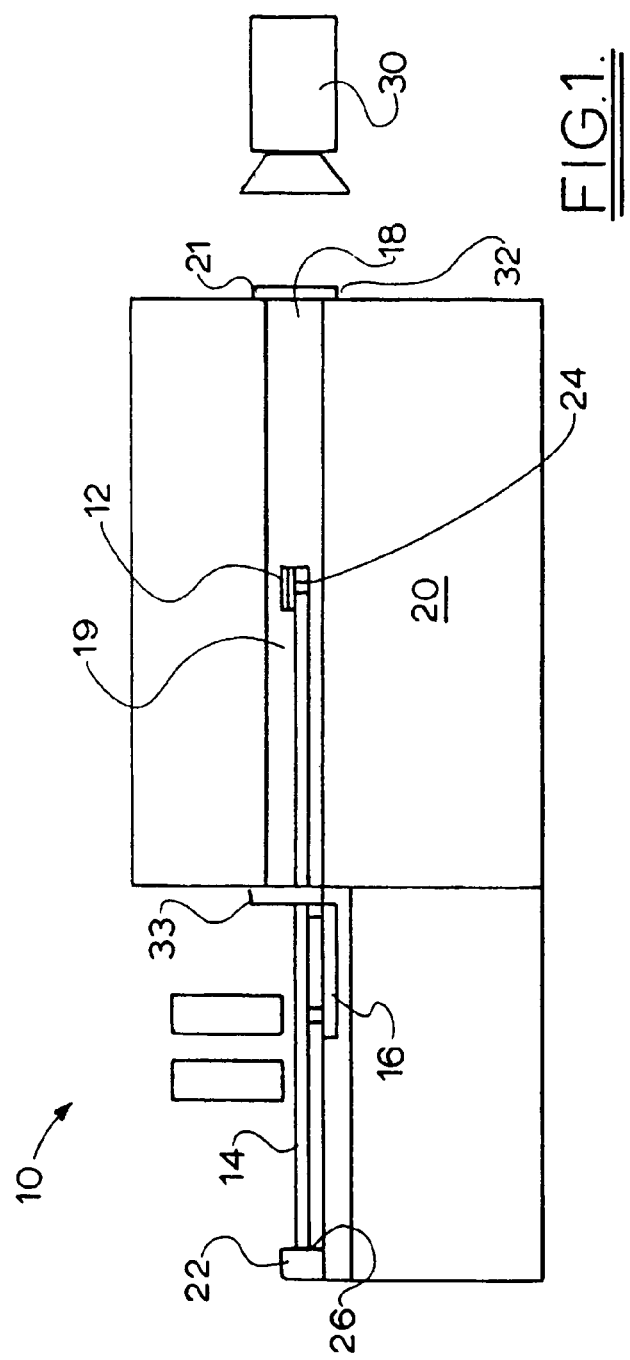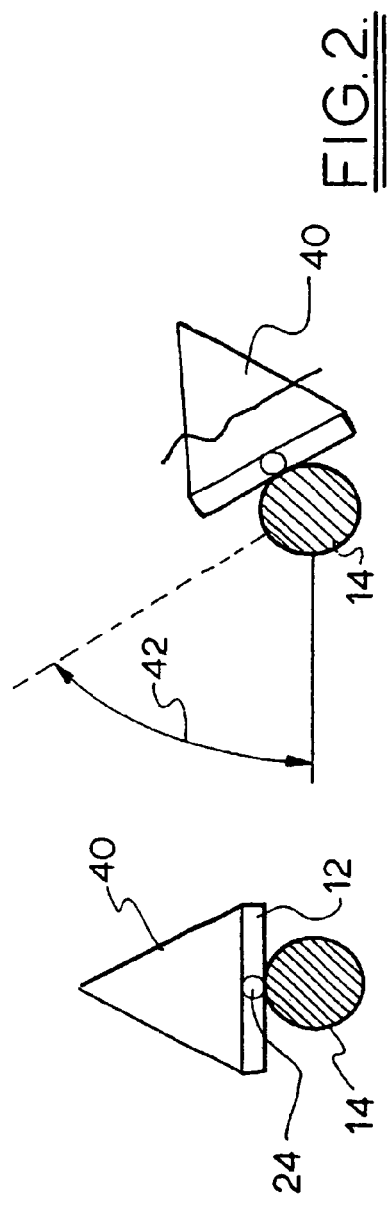
FIG.1.
FIG.2.

METHOD FOR DETERMINING STICKING AND FLOW PROPERTIES OF PARTICULATE SOLIDS

CROSS REFERENCE TO RELATED AND PRIORITY APPLICATION

This application is a divisional of Ser. No. 10/451,093 filed Jun. 18, 2003, now U.S. Pat. No. 6,845,680 B2, which is a national phase of PCT International Application No. PCT/AU01/01657 filed on Dec. 21, 2001. The PCT International Application was published in English on Jul. 4, 2002 by the International Bureau.

FIELD OF THE INVENTION

This invention is concerned generally with the problems of adhesion, sticking, agglomeration or sintering of particulate solids in processes operating at elevated temperatures. Of particular interest for the purpose of this application are processes involving pyrometallurgical processing of particulate minerals where adhesion or agglomeration of the particles impedes process efficiency or throughput, for example in fluidised beds, rotary kilns or rotary hearth furnaces.

The invention is described with particular reference to the specific example of the direct reduction of fine iron oxides to iron in one or more interconnected furnaces. Such processes are generally known as direct reduction of iron processes (DRI). Although the example used here is for DRI, it is emphasised, however, that the invention, has broad application to processes operating at elevated temperatures involving the presence of particulate solids.

BACKGROUND ART

It is a general feature of processes of the kind in question that changes in particulate properties (chemical or physical), and/or changes in process conditions which lead to adhesion or sticking of particles either to each other or to process equipment, can lead to a decrease in process efficiency (for example through decreased mixing and mass transfer in fluidised beds or kilns) or process throughput (for example through interruptions to flow of the particulate solids within or between reactor vessels). Also, in some processes there can be a gradual agglomeration or sintering of particulate solids that can interrupt the process requiring corrective action, and eventually decreases the process capability to the extent that it has to be shut down for a period to allow physical removal of the accretions formed.

Examples of DRI processes in which particulate stickiness, adhesion and flow properties are key factors, include the FIOR™, FINMET™, FINEX™ and SL/RN kiln processes.

It is known that both process conditions and properties of the particulate solids influence the degree of stickiness or adhesion. The readiness or otherwise with which particulate solids in a process tend to stick or adhere to each other or process equipment is sometimes expressed qualitatively in terms of the "stickiness" of the solids for the particular conditions in question, but to date there has been no method for providing a reliable, quantitative measure of this quality. Particulate solids, eg iron-containing fines, appear in some conditions to have a particular disposition to be sticky, which can, for example, lead to "bogging" or defluidisation in fluidised beds, poor solids flow between process vessels, and formation of accretions in fluidised beds and rotary kilns.

To date, there has been no reliable measure to quantify this "stickiness" and it has proven difficult to predict the adhesion, stickiness or agglomeration behaviour of particulate solids impacting the process performance (efficiency, throughput and availability). This is particularly the case for higher temperature processes involving mineral particles, where complex phases exist that influence particulate behaviour, and to manage this stickiness/adhesion behaviour and/or accretion formation has involved somewhat imprecise empirical methods. These have been less than satisfactory given the wide number of parameters that appear to be involved.

Several investigations have attempted to simulate the real behaviour of particulate solids during direct reduction of iron ores using laboratory scale fluidised bed reactors in conjunction with optical and/or scanning electron microscopy, eg, Gransden and Sheasby (1974), Astier and Roux (1975), Hyashi and Iguchi (1992), Janssen (1994), Gudenau et al (1997). These test methods rely on being able to simulate the gas, temperature, chemical reaction rates and fluid dynamic conditions in a process. As this is rarely possible, the tests give only a qualitative comparison of sticking behaviour. Mikami et al (1996) followed a similar procedure to investigate sticking during the manufacture of iron powder for powder metallurgy. The apparatus for these tests is complex and large samples are typically required.

Other workers have utilised standard ash fusion and compression tests to estimate the agglomeration tendency of ash in fluidised bed combustors, eg Conn (1994), and Skrifvars et al (1999). However, these tests do not have a flow component and therefore tend to overestimate the agglomeration temperature.

Conn (1994) proposed a drained angle of repose test which measured the flow properties of approximately 1.4 kg of sample under appropriate temperature conditions. This test has the advantage of measuring flow properties, but requires large samples and it may be difficult to provide a controlled gas atmosphere.

Papers Mentioned Above

Astier and Roux, "Comments on the Application of Fluidisation to Prereduction of Iron Ore", Revue de Metallurgie, October 1975, pp 755,778.

Conn., "Laboratory Techniques for Evaluating Ash Agglomeration Potential in Petroleum Coke Fired Circulating Fluidized Bed Combustors", Fuel Processing. Technology, Vol 44 (1995), pp 95,103.

Gransden and Sheasby, "The Sticking of Iron Ore During Reduction by Hydrogen in a Fluidized Bed", Canadian Metallurgical Quarterly, Vol 13, No 4 (1974), pp 649,657.

Gudenau et al, "Process technology problems during the direct reduction of fine iron ore in a fluidised-bed with hydrogen-rich gas" Institut Eisenhuttenkunde, RWTH Aachen, Stahl Eisen (1997), 117(4), 91-99.

Hyashi and Iguchi, "Factors Affecting the Sticking of Fine Iron Ores during Fluidized Bed Reduction", ISIJ International, Vol 32, No 9 (1992), pp. 962,971.

Janssen, "The Effect of Carbon and Sulphur on the Sticking Behaviour of Fine Ores During Metallisation in the Fluidised Bed", PhD Thesis, Aachen Rhenian-Westphalian Technical university, 1994.

Mikami et al, "The Mechanism of Defluidization of Iron Particles in a Fluidized Bed", Powder Technology 89 (1996), pp 231,238.

Skrifvars et al, "Predicting Bed Agglomeration Tendencies for Biomass Fuels Fired in FBC Boilers: A Comparison of Three Different Prediction Methods", Energy and Fuels, Vol 13, No 2 (1999), pp 359, 363.

SUMMARY OF THE INVENTION

It is an objective of the invention to address the above described difficulties with a view to obtaining a reliable, quantitative measure of the "stickiness" of the particulate solids under: process conditions of temperature and gas composition, and to use this quantitative measure to better manage processes involving particulate solids at elevated temperatures. The invention provides a simple test to yield a quantitative measure of particulate stickiness or adhesion properties which may influence the flow, fluidisation and accretion properties of the particulate solid, requires a relatively small sample, and can reliably reproduce the appropriate mechanisms of sticking under actual process conditions of temperature and gas atmosphere. This invention can be used to determine the influence of both the particulate properties (eg size, chemistry, shape) and process conditions (eg temperature and gas composition) on the quantitative measure of stickiness and hence on the efficiency of the desired process being investigated.

It is a further preferred objective to apply these techniques to enhance fines-based DRI processes.

In a first aspect, the invention proposes a novel quantitative measure of the "stickiness"or adherence properties of heated particulate solids that is readily adaptable to the testing of samples from different process locations while simulating process conditions and is adaptable to reproduce the relevant mechanisms of sticking. Importantly, the method and apparatus will permit enhanced management and control of processes involving particulate solids at temperature and under process gas compositions.

In this first aspect, therefore, the invention provides a method of obtaining a measure of the stickiness of heated particulate solids, including:

depositing a sample of the particulate solids on a generally horizontal support by pouring the sample onto the support and allowing it to freely form its own angle of repose;

subjecting the sample to a predetermined heating regime and gas atmosphere; and rotating the support about an axis having a generally horizontal component to an angular position at which integrity of the sample fails, which angular position is a measure of the stickiness of said particulate solids.

The invention further provides in its first aspect, apparatus for obtaining a measure of the stickiness of heated particulate solids, including:

a support for receiving a sample of the particulate solids while generally horizontal, by pouring the sample onto the support and allowing it to freely form its own angle of repose;

means to subject the sample to a predetermined heating regime and gas atmosphere; and means to rotate the support about an axis having a generally horizontal component to an angular position at which integrity of the sample fails, which angular position is a measure of the stickiness of said particulate solids.

Preferably, the method in the first aspect of the invention extends to include monitoring and preferably control of a process involving the heated particulate solids, wherein a measure of the stickiness of the heated particulate solids is obtained at intervals, and the process managed and/or controlled in dependence on said measure of stickiness.

In a particular application, the particulate solids include iron-containing particles, eg. fines, in which case the said heating regime comprises heating the particles to a temperature in the range 400 to 1000° C. in the presence of an appropriate atmosphere. For direct reduction of iron this may be a gas mixture containing hydrogen and/or carbon monoxide. Oxidising gasses are also useful to simulate process interruptions.

In a second aspect of the invention, it has been realised that there is a critical temperature transition for the stickiness of iron-containing particulate solids.

More specifically, the invention, in its second aspect, provides a method of enhancing the control and efficiency of a DRI process, including:

determining, at one or more locations in the process, one or more critical temperature transitions for the stickiness of iron-containing particulate solids; and controlling one or more parameters of the process (eg gas and/or solids temperatures and/or compositions) at said one or more locations and/or at one or more other locations in the process, in order to maintain the process conditions at said one or more locations in a favourable range with respect to said critical temperature transition(s).

BRIEF DESCRIPTION OF THE DRAWINGS

The invention will be further described, by way of example only, with reference to the accompanying drawings, in which:

FIG. 1 is an axial cross-sectional diagram of testing apparatus for obtaining a measure of the stickiness of heated particulate solids, according, to an embodiment of the first aspect of the invention;

FIG. 2 is a simple diagram illustrating the principle linking the quantitative measure of stickiness with the operation of the apparatus of FIG. 1;

PREFERRED EMBODIMENTS

Figure 3:
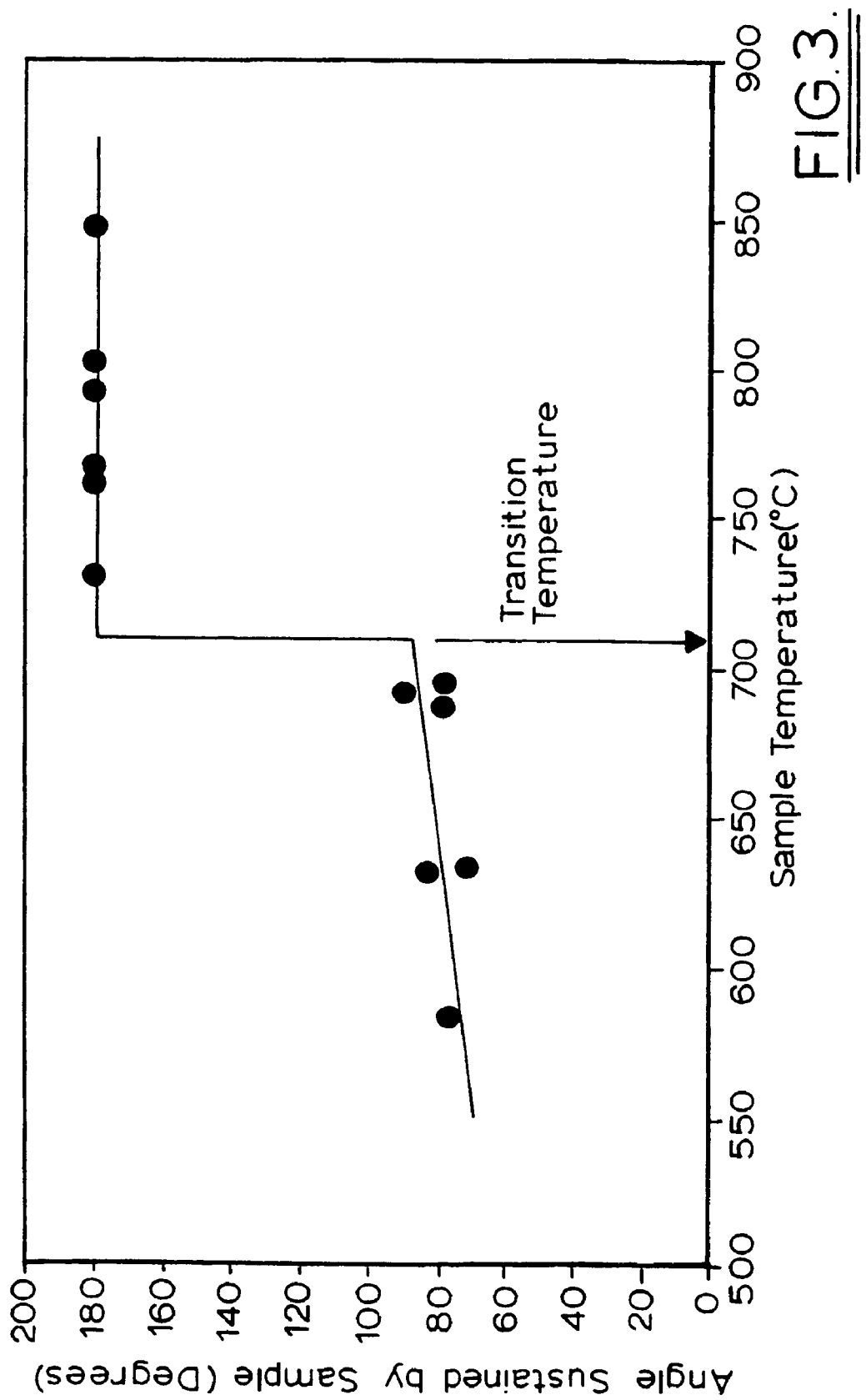
FIG. 3 is an example of transition temperature determination for a DRI sample by plotting the angle that the sample can sustain during rotation against the sample temperature.

The testing apparatus 10 illustrated in FIG. 1 includes a sample support 12 fitted atop an elongate translator rod 14 at one end of the rod. Sample support 12 comprises a simple rectangular dish with an upstanding shallow peripheral edge lip. Rod 14 is, supported on a sliding bearing 16 positioned for placing the sample support in the tubular heating cavity 18 of a furnace 20. Rod 14 is rotatable manually or using an electric motor 22 outside the furnace.

A suitable furnace 20 is a horizontal tube furnace, in which the gas atmosphere in the heating cavity is controlled by continuously purging with an appropriate gas mixture via rotameter gas inlet 21. The furnace temperature is controlled using a programmable controller referenced to an appropriate thermocouple placed near the sample support location in the hot zone 19 of the furnace. The sample temperature is measured using an appropriate thermocouple 24 mounted in the base of sample support 12.

The normal at-rest position of sample support 12 is with its base substantially horizontal. When it is rotated by motor 22, the angular displacement of the sample support from the horizontal is measured using a linear potentiometer connected at 26 to the end of rod 14. Manual rotation of the sample may also be used in the absence of a motor. The test number, sample identification, instantaneous time, angular position and temperature of the sample (determined by thermocouple 24) are superimposed on a video record of the sample made with a video camera 30. Camera 30 is aligned coaxially with furnace cavity 18 to view the sample from outside the furnace on the side opposite that from which rod 14 projects. The sample angle may also be visually determined rather than by camera. The gas seal at this end 32 is transparent to facilitate viewing with camera 30.

The manner is which a typical stickiness test may be carried out will now be described. A sample 40 (FIG. 2) of a fine particulate solid such as iron-containing fines is deposited on sample support 12 by pouring the sample onto the support and allowing it to freely form its own angle of repose. A convenient sample size is 10-15 g. The pouring step can be accomplished in a consistent manner by positioning a small funnel on the sample support, pouring the entire sample into the funnel and then lifting the funnel vertically away from the sample support, allowing the sample 40 to form its own angle of repose on the base of the sample support.

The sample support with its sample 40 in place is then slid along cavity 18 to a central position in the hot zone 19 of the furnace without vibration so as to prevent, settling of the sample. Oxygen is expunged and an inert atmosphere substituted in cavity 18, and the gas seals 32, 33 applied. Where desired, a suitable atmosphere can then be circulated through the furnace cavity, eg. a reducing atmosphere such as an atmosphere of hydrogen and/or carbon monoxide or hydrogen with nitrogen. Oxygen should typically be excluded since oxygen accelerates sintering conditions.

An appropriate time is allowed for the sample to reach the desired temperature: this selection is made in dependence upon the nature of the sample and on any comparative issues with other tests and will vary from case to case. Both the video camera 30 and the electric motor 22 are then activated and the sample support is slowly rotated by up to 180° (FIG. 2). It is found that the integrity of the sample will fail, ie. a proportion of the sample will collapse and fall away from the remaining sample on the support, relatively suddenly and the angular position 42 at which this occurs can bedetermined by playback of the video image. The angular position is taken as a quantitative measure of the stickiness of the particulate solid of the sample.

When the apparatus of FIG. 1 was employed for testing the stickiness of partially or wholly reduced iron extracted from different locations of the DRI process, certain observations were made. At low temperatures, the samples flowed at relatively low angles of rotation. At higher temperatures, eg. above 500° C., a crust formed on the outside; of the DRI pile, and a higher angle was necessary to generate the stresses required for this crust to fail. In some cases the DRI sample was sintered to the extent that the sample support could be turned wholly upside down without the integrity of the DRI crust failing.

As mentioned earlier, it has been realised through use of the testing apparatus of FIG. 1 that there is a critical temperature transition for the stickiness of iron-containing particulate solids. FIG. 3 is a: simple diagram showing the transition temperature measured for a sample of DRI by plotting the angle that the sample can retain during rotation against transition temperature. An angle of 180° means that the sample remained attached to the sample support when completely upside down. The transition temperature, where the sample becomes sticky, is evident as a step in the curve of the plot. The transition temperature indicated by FIG. 3 is not taken as a direct simulation of sticking behaviour in the process, where the mechanical and fluid dynamic conditions may vary from the test conditions. However, the, test was run under conditions that reproduced the relevant mechanism of sticking, eg, sintering of metallic iron. Trends in transition temperature with sample type or test conditions therefore reproduce trends in agglomeration behaviour in the process.

Figure 4:
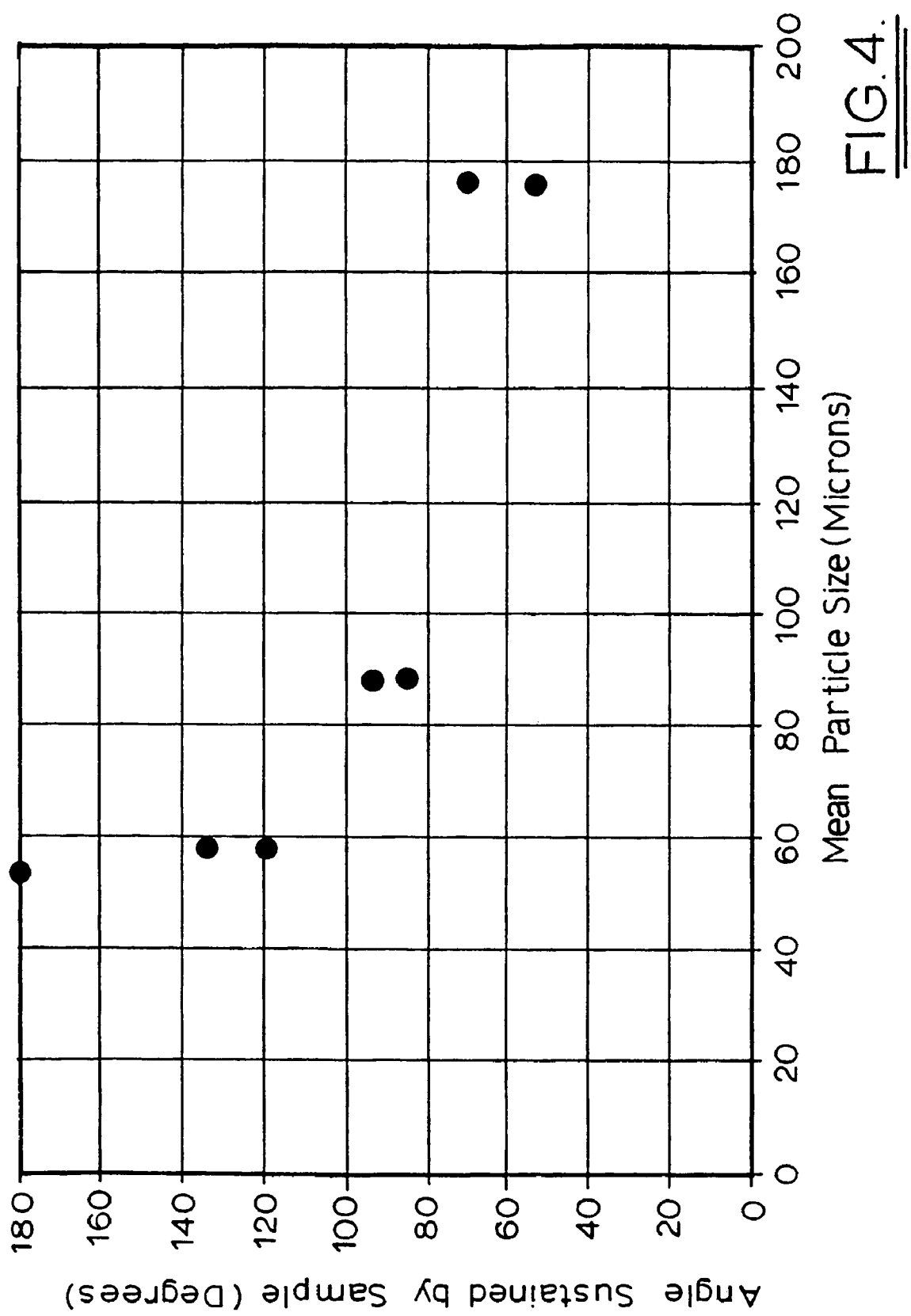
FIG. 4 is a graph illustrating the angle sustained by a sample type with varying particle size distribution.

FIG. 4 is a graph illustrating the increase in stickiness of a sample, measured by the increase in the angle sustained by the sample during rotation, with decreasing mean particle size. As the particles in the process become finer, the surface area per unit volume increases, increasing the stickiness of the sample under fixed conditions of temperature and gas atmosphere.

Figure 5:
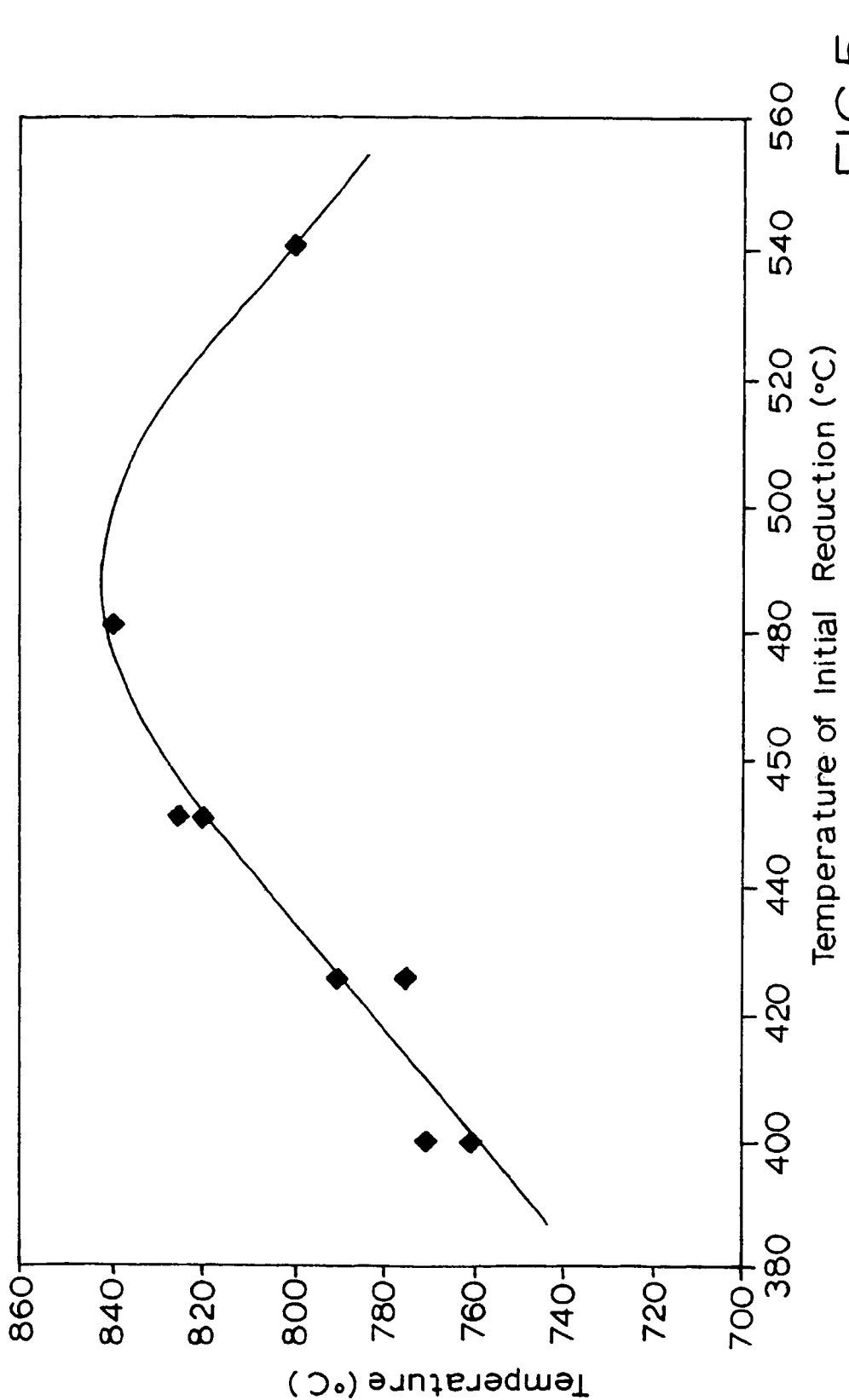
FIG. 5 is a graph illustrating how the stickiness transition temperature (measured with the apparatus of FIG. 1) of samples extracted from a direct reduction process varies with the initial temperature of reduction of the iron ore. This is an example of how the invention can be used to enhance the control of the reduction profile in a DRI process.

FIG. 5 is a graph illustrating the observed relationship of sticking transition temperature (measured with the apparatus of FIG. 1) for samples extracted from a DRI process with changes in the temperature of initial reduction. It will be seen that there is an optimum temperature of initial reduction for maximising the sticking transition temperature in the process, ie. for minimising the stickiness of the solids, which in this case is in the region of 460-500° C. As the initial reduction temperature is reduced from this region, the material becomes progressively more sticky in the sense that the stickiness transition temperature decreases. For the iron oxide in this particular process, this is believed to be linked to the formation and nature of surface iron on certain particles.

It is envisaged that the inventive apparatus may be employed to monitor and manage a DRI process by regularly extracting samples for testing of stickiness from several locations in the process, eg. from each reactor and perhaps from each reactor-reactor solids transfer passage. These samples would typically be allowed to cool under an inert atmosphere to avoid reoxidation, and then tested utilising the apparatus. For a particular process, such testing would allow accumulation of data and knowledge concerning the process and permit the control of a process parameter, especially temperature, at one or more selected locations in the process in order to maintain the temperature of the iron-containing solids at those or other locations in a favourable range with respect to the known critical transition temperatures for stickiness. The potential for this to substantially enhance a DRI process and allow a significant improvement in process efficiency and control is demonstrated by the results in FIG. 4.

The method is particularly suitable to processes where fine particulate solids, eg −1 or −2 mm, are responsible for sticking/agglomeration, however, no limits are placed on the size; of the other particulate solids present in the process. It is thought that the general concept of the method may be adapted, for example, to test particulate solids having particle sizes up to 10 mm, or at least up to 5 mm.

The invention claimed is:

1. A method of operating a direct reduction of iron process, in which iron-containing particulate solids are treated at elevated temperatures in order to reduce iron oxides in the solids, the method comprising:

extracting, at at least one location in the direct reduction of iron process, a sample of said iron-containing particulate solids;

determining from said sample a transition temperature at which the stickiness of the iron-containing particulate solids exhibits a critical transition; and controlling at least one parameter of the direct reduction of iron process at a controlled location in the process in order to maintain the temperature of the iron-containing particulate solids at the at least one location in the process from which the sample is extracted in a favourable range with respect to the transition temperature at which the stickiness of the iron-containing particulate solids exhibits a critical transition.

2. A method according to claim 1 wherein said at least one parameter is selected from gas and solids temperatures and gas and solids compositions.

3. A method according to claim 1 wherein said at least one parameter includes a temperature of initial reduction.

4. A method according to claim 1 wherein said controlled location in the process is said at least one location from which the sample is extracted.

5. A method according to claim 1 including extracting respective samples of the iron-containing particulate solids at a plurality of locations in the direct reduction of iron process, and determining for each such location a transition temperature at which the stickiness of the iron-containing particulate solids exhibits a critical transition.

6. A method according to claim 1 wherein said transition temperature at which the stickiness of the iron-containing particulate solids exhibits a critical transition is determined by:

depositing said sample on a generally horizontal support by pouring the sample onto the support and allowing it to freely form its own angle of repose;

subjecting the sample to a predetermined heating regime and gas atmosphere;

rotating the support about an axis having a generally horizontal component to an angular position at which integrity of the sample fails;

plotting the angles at which integrity of the sample fails against sample temperatures, which angular position is a measure of the stickiness of said particulate solids; and identifying as the transition temperature that temperature at which there is a step in the plot.

7. A method according to claim 6 wherein said predetermined heating regime comprises heating the particles to a temperature in the range of 400 to 1000° C. in an appropriate atmosphere.

* * * * *

UNITED STATES PATENT AND TRADEMARK OFFICE
CERTIFICATE OF CORRECTION

PATENT NO. : 7,615,098 B2  Page 1 of 1
APPLICATION NO. : 11/025339
DATED : November 10, 2009
INVENTOR(S) : Brent et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 373 days.

Signed and Sealed this

Nineteenth Day of October, 2010

David J. Kappos
*Director of the United States Patent and Trademark Office*